United States Patent [19]

Doore et al.

[11] 4,012,795

[45] Mar. 22, 1977

[54] ARTIFICIAL HEAD ASSEMBLY FOR AN ARTICULATED JOINT BETWEEN TWO BONES

[75] Inventors: Erhard Dörre, Plochingen, Germany; Manfred Semlitsch; Otto Frey, both of Winterthur, Switzerland

[73] Assignee: Feldmuhle Anlagen- und Produktionsgesellschaft mit beschrankter Haftung, Germany

[22] Filed: Oct. 29, 1975

[21] Appl. No.: 626,733

[30] Foreign Application Priority Data

Oct. 29, 1974 Germany .......................... 2451275

[52] U.S. Cl. .................................. 3/1.91; 3/1.913; 128/92 CA
[51] Int. Cl.² ........................................ A61F 1/24
[58] Field of Search ...................... 3/1.9–1.913, 3/1; 128/92 C, 92 CA

[56] References Cited

UNITED STATES PATENTS 3,894,297  7/1975  Mittelmeier et al. ............... 3/1.912

FOREIGN PATENTS OR APPLICATIONS 1,017,927  10/1952  France ......................... 128/92 CA
1,334,584  10/1973  United Kingdom ............. 128/92 C Primary Examiner—Ronald L. Frinks
Attorney, Agent, or Firm—Hans Berman

[57] ABSTRACT

An artificial head assembly for a human femur consists of the head portion proper and a metal pin. The head portion is a sintered ceramic ball having a polished contact face of convex, spherical curvature and a blind bore tapering conically inward toward the contact face. The pin is shaped for insertion of one end into the hollow stump of the femur, the other end tapering conically at the same apex angle as the bore in the ball. A knurling of the conical face of the pin reduces the compressive strength of the pin surface to less than the tensile strength of the ball so that the assembled head and pin can be sterilized without cracking the ceramic head portion because of differences in coefficients of thermal expansion between the metal and the ceramic material.

9 Claims, 2 Drawing Figures

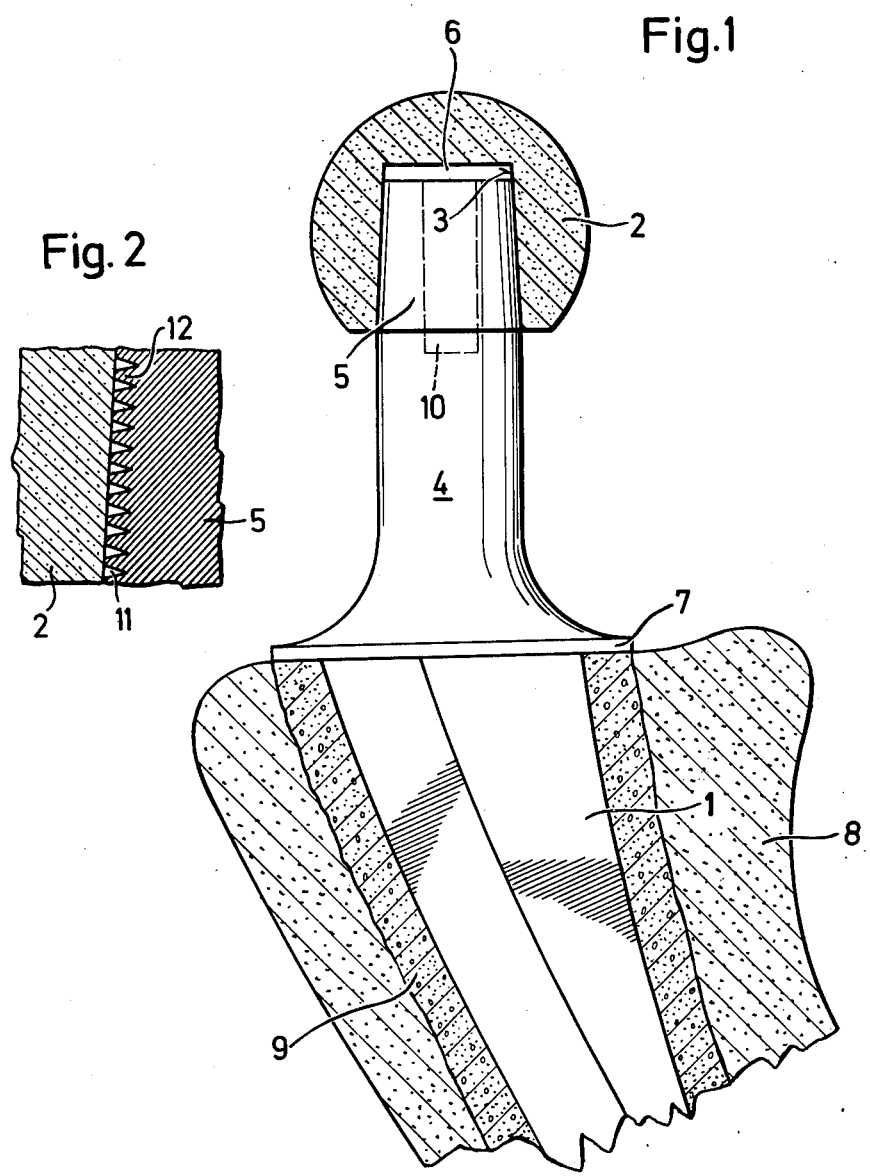

ARTIFICIAL HEAD ASSEMBLY FOR AN ARTICULATED JOINT BETWEEN TWO BONES

This invention relates to artificial, articulated joints between two bones, and particularly to a head assembly for such a joint.

Artificial femur heads are frequently implanted after fractures or other defects of the femur, and convexly curved heads of other bones also are replaced surgically for cooperation with an available natural or implanted artificial concavity of another bone. The invention will be described hereinafter with reference to a hip joint and its elements because of the predominance of surgical hip joint repairs by implantation of artificial femur heads. It should be understood, however, that the invention is not limited to any specific bone, nor to human bones.

It has been proposed heretofore to shorten the diseased or fractured femur, and to fasten an artificial head assembly in the longitudinal cavity of the stump, the assembly essentially consisting of an elongated fastening portion, hereinafter referred to as a pin, and of a head portion proper which is approximately spherically curved for articulated engagement with a concavely arcuate surface of a pelvic bone.

The stresses encountered in service by the pin and head are different, and a satisfactory single material of construction for both portions of the assembly is not yet available. Although certain alloys compatible with human tissue have been employed for both the pin and head, such implants have been found to provide a head of limited useful life.

It has been proposed to implant head assemblies consisting of a ceramic head portion fastened to a metallic pin (German patent application No. P 21 34 316.8, laid open Jan. 13, 1972) by a quick-setting methyl methacrylate cement. Such cements are not fully resistant to the environment which they encounter in service, and may be resorbed, thereby weakening or releasing the bond between the elements of the head assembly. A head capable of moving relative to the pin may irritate adjacent tissue and require replacement of the femur head.

While the ceramic material recommended for the known head assemblies, sintered aluminum oxide, is eminently suitable for a head portion of practically unlimited service life, and several known alloys have all necessary properties for a pin, the problem of attaching the two portions to each other without the use of a potentially unreliable cement remained unsolved heretofore. Artificial femur heads of the known types were implanted heretofore almost exclusively in elderly patients having a relatively short life expectancy.

It was proposed in the German patent application No. P 20 59 381.1, laid open on Mar. 9, 1972, to make the two portions of a head assembly for a hip joint of plastic and of metal respectively, and to join the head portion to the pin by means of a conically tapering end portion of the pin engaged in a conforming bore of the head portion. The connection is self-tightening under the tension of the muscles connecting the thigh to the trunk and under the weight of the patient, but still permits the head to be replaced as may be needed when the plastic material is worn out.

A ceramic head portion and a metal pin cannot normally be assembled in the same manner prior to implantation because of the difference between the coefficients of thermal expansion of sintered aluminum oxide or other ceramic material suitable for the head portion and of the metals of adequate strength, corrosion resistance and compatibility with body tissues which are known at this time or may be expected to become available in the near future. When an assembly including a conical end of a metal pin and a ceramic head portion formed with a cavity conformingly receiving the pin is sterilized by heating prior to implantation, the metal expands so much more than the ceramic material that the head portion may be either destroyed during sterilizing or damaged by the imposed tensile stress so as to fail in service. It is not practical separately to sterilize the two parts of the assembly and to combine them under sterile conditions while the patient is on the operating table. For adequate strength of the connection, the component parts must be force-fit using equipment hardly capable of being kept sterile.

It is an object of the invention to provide an artificial head assembly for a hip joint or other articulated joint between two bones in which a metal pin is fixedly fastened to a ceramic head portion by means of mating male and female conical portions in the manner described, yet is capable of being sterilized by heat without mechanical damage to the ceramic head portion.

According to a more specific aspect of the invention, the conically tapering end portion of the pin consists of a metal whose coefficient of thermal expansion is much greater than that of the ceramic material of the head, such as sintered aluminum oxide, and the metallic end portion is received in a blind bore of the head portion which tapers conically inward at an apex angle substantially identical with that of the metal, the metal and ceramic material being in direct contact along a conical interface extending preferably over almost the entire depth of the bore, but at least over more than one half of the bore depth.

Sterilization of the head assembly without damage by thermal stresses can be achieved with any combination of materials by reducing the crushing strength or resistance to deformation of a surface layer of one material to less than the strength of the main portion of the same material and preferably to less than the strength of the engaged surface layer of the other material. The thermal stresses generated at the interface during sterilization cause deformation of the weaker surface layer. If the pin was driven into the head portion prior to sterilization for a strong friction fit, but without deforming the weaker surface layer to the limit, the force holding the head portion to the pin is weakened by sterilization, but remains sufficient for implantation and for initial use of the implanted head assembly. Loading of the joint by the patient's weight further strengthens the connection.

The afore-mentioned surface layer may be weakened by reducing its bulk density or overall specific gravity, as by forming the surface layer with recesses which reduce the contact area between the two materials to the lands between the recesses. Stress is concentrated on these lands which are dimensioned to yield under the thermal sterilization stresses.

It is possible, though costly and difficult, to modify the ceramic surface in the bore of the head portion in a manner to reduce its crushing strength, and it is generally preferred to weaken the surface layer of the metallic pin by machining or by chemical or electric etching.

After initial assembly, and during subsequent thermal sterilization, implantation, and use, the pin and head portion engage each other in a conically tapering interface over most of the depth of the bore in the head portion, but the contact area may be smaller than the overall area of the interface without impairing the strength of the bond, basically a friction bond, between the constituent materials.

Other features, additional objects, and many of the attendant advantages of this invention will readily be appreciated from the following detailed description of a preferred embodiment when considered in connection with the appended drawing in which:

FIG. 1 shows an artificial head assembly of the invention attached to a femur stump in fragmentary elevation, partly in section; and FIG. 2 illustrates the interface of the head portion and pin in the assembly of FIG. 1 in greatly enlarged elevational section.

Referring initially to FIG. 1, there is seen a pin of conventional shape embedded in the central cavity of a femur stump 8 by means of a methacrylate cement 9. The cement is sealed in the femur by means of an integral shoulder 7 on the pin. The integral portion 4 of the pin 1 which projects beyond the shoulder 7 is cylindrical near the shoulder and terminates in a conically tapering end portion 5. It is conformingly received in a bore 3 of a spherically curved head portion 2.

The latter consists of sintered aluminum oxide containing more than 99.7% $Al_2O_3$, a grain size of less than 8 $\mu m$, and a specific gravity greater than 3.90. The high purity is essential for good compatibility with body tissue and high corrosion resistance, the small grain size and the high density permit the convex, spherical face of the head portion 2 to be polished to a finish important for practically frictionless engagement with a cooperating socket. A preferred material for the pin 1 is the known alloy whose nominal composition is 20% Cr, 35% Ni, 33% Co, 10% Mo, 1% Ti, and 1% Fe, which combines desirable mechanical and chemical properties and is capable of being forged to the desired shape.

The apex angle of the cone defined by the end portion 5 is substantially identical with that defined by the ceramic walls of the bore 3 and is approximately 4° although shown greater in the drawing for the convenience of pictorial representation. The angle should amount to 2°30′ to 6°.

In the assembled condition prior to loading, as shown in FIG. 1, the axial length of the conical interface between the end portion 5 and the ceramic wall of the bore 3 is almost as great as the axial depth of the blind bore 3, only about 10% of the axial bore length at the inner end of the bore forming an expansion chamber 6 for further penetration of the pin 1 into the head portion 2 after contact with the socket of the pelvic bone under the weight of the patient. An axial bore 10 extends inward of the pin 4 from the chamber 6 into the cylindrical pin portion. It enhances the resiliency of the end portion 5 and thereby facilitates conforming engagement between the head portion 2 and the pin 1, also helps absorb some of the thermal stresses during thermal sterilization.

Such stresses are absorbed mainly in the weak, integral layer of metallic material which constitutes the surface of the conical end portion 5. As is better seen in the enlarged sectional view of FIG. 2, the conical surface is formed with recesses 11, more specifically, with two groups of intersecting, shallow grooves having an approximately V-shaped cross section so that the frustoconical surface of the end portion 5 appears finely knurled. The knurling is not readily recognizable on the scale of FIG. 1 and has not been shown there. The initial dimensions of the grooves 11 are chosen to permit partial deformation of the intervening ribs 12 under thermal sterilization stresses without transmitting harmful tensile stresses to the ceramic material of the head portion 2. For a head portion dimensioned for use in the hip joint of an average adult and otherwise as illustrated, the depth of the grooves 11 may be approximately 0.01 to 0.025 mm.

While a pin 1 fastened in a femur stump 8 by means of cement 9 has been shown in FIG. 1, the invention, of course, is equally applicable to pins inserted in the bone cavity without any cement and fastened by direct engagement with the bone. Even in the illustrated embodiment, the cement is gradually replaced by tissue during use of the head assembly in a manner not available with cement interposed between a metallic pin and a ceramic head portion.

It should be understood, therefore, that the foregoing disclosure relates only to a preferred embodiment of the invention, and that it is intended to cover all changes and modifications of the example of the invention chosen for the purpose of the disclosure which do not constitute departures from the spirit and scope of the invention set forth in the appended claims.

What is claimed is:

1. An artificial head assembly for an articulated joint between two bones comprising:
    a. an elongated pin member having a conically tapering longitudinal end portion of metallic material; and
    b. a head portion of ceramic material having a substantially spherical, convex engagement face and formed with a blind bore conically tapering inward of said head portion at an apex angle substantially identical with the apex angle of said tapering end portion,
        1. said ceramic material and said metallic material directly engaging each other in a conically tapering interface extending over more than one half of the axial length of said bore,
        2. said head portion being fixedly fastened to said pin member by said engaged materials,
        3. one of said materials having a surface layer contiguously adjacent said interface and a main portion separated from said interface by said surface layer,
        4. the resistance to deformation of said surface layer being smaller than the resistance to deformation of said main portion.

2. An assembly as set forth in claim 1, wherein said end portion is formed with a cavity therein.

3. An assembly as set forth in claim 1, wherein said ceramic material is aluminum oxide containing at least 99.7% $Al_2O_3$, having a specific gravity of at least 3.90, and a grain size not greater than 8 $\mu m$.

4. An assembly as set forth in claim 1, wherein said apex angles each are between 2°30′ and 6°.

5. An assembly as set forth in claim 1, wherein said one material is said metallic material, and said surface layer is formed with a plurality of recesses defining lands of said material therebetween.

6. An assembly as set forth in claim 5, wherein said recesses constitute two groups of transversely intersecting grooves in said surface layer.

7. An assembly as set forth in claim 5, wherein said end portion is formed with a longitudinal bore extending inward of said pin member.

8. An artificial head assembly for an articulate joint between two bones comprising:
 a. an elongated pin member having a conically tapering longitudinal end portion of metallic material; and
 b. a head portion of sintered aluminum oxide having a substantially spherical, convex engagement face and formed with a blind bore conically tapering inward of said head portion at an apex angle substantially identical with the apex angle of said tapering end portion,
 1. said metallic material having a coefficient of thermal expansion greater than the coefficient of thermal expansion of said aluminum oxide,
 2. said aluminum oxide and said metallic material directly engaging each other in a conically tapering interface extending over more than one half of the axial length of said bore,
 3. said head portion being fixedly fastened to said pin member by said engaged materials.

9. An assembly as set forth in claim 8, wherein one of said materials has a surface layer contiguously adjacent said interface and a main portion separated from said interface by said surface layer, the resistance to deformation of said surface layer being smaller than the resistance to deformation of said main portion.

* * * * *